(12) United States Patent
Resch et al.

(10) Patent No.: US 12,390,207 B2
(45) Date of Patent: Aug. 19, 2025

(54) SURGICAL RETRACTOR DEVICE

(71) Applicant: Viking Arm Medical AS, Baerums Verk (NO)

(72) Inventors: Øivind Resch, Oslo (NO); Hans Martin Aguilera, Oslo (NO); Terje Scheen, Drøbak (NO); Ivar Bjarne Mo, Vear (NO)

(73) Assignee: Viking Arm Medical AS, Baerums Verk (NO)

( * ) Notice: Subject to any disclaimer, the term of this patent is extended or adjusted under 35 U.S.C. 154(b) by 157 days.

(21) Appl. No.: 18/278,727

(22) PCT Filed: Feb. 23, 2022

(86) PCT No.: PCT/NO2022/050050
§ 371 (c)(1),
(2) Date: Aug. 24, 2023

(87) PCT Pub. No.: WO2022/182247
PCT Pub. Date: Sep. 1, 2022

(65) Prior Publication Data
US 2024/0138825 A1    May 2, 2024

(30) Foreign Application Priority Data

Feb. 26, 2021  (NO) .................................. 20210268

(51) Int. Cl.
*A61B 17/02* (2006.01)
*A61B 17/00* (2006.01)

(52) U.S. Cl.
CPC .. *A61B 17/0206* (2013.01); *A61B 2017/0046* (2013.01); *A61B 2017/00539* (2013.01)

(58) Field of Classification Search
CPC .................... A61B 17/0206; A61B 2017/0046
(Continued)

(56) References Cited

U.S. PATENT DOCUMENTS 10,603,025 B2    3/2020  Sauer
2005/0234304 A1  10/2005 Dewey et al.
(Continued)

FOREIGN PATENT DOCUMENTS

CN    110974321 A    4/2020
EP    2 080 480 A1   7/2009
(Continued)

OTHER PUBLICATIONS

International Bureau, International Preliminary Report on Patentability issued in International Patent Application No. PCT/NO2022/050050 on Aug. 29, 2023.
(Continued)

*Primary Examiner* — Eduardo C Robert
*Assistant Examiner* — Tara Rose E Carter
(74) *Attorney, Agent, or Firm* — Leydig, Voit & Mayer, Ltd.

(57) ABSTRACT

A surgical retractor device has a housing with press arms coupled thereto, each arm having rotational movement in a plane, and a gripping member pivoting at right angle with the plane, at an outer end of the arm; an attachment means at an inner end of the arm; an opening and closing mechanism with rotatable press arm attachment structures attaching the attachment means of the press arms, symmetrically positioned from a centerline of the device; rotatable handle attachment structures, and; a transfer mechanism transferring rotation from handle attachment structures to press arm attachment structures. The device also has handles for operating the opening and closing mechanism. Each handle has a handle attachment means at an inner end of the handle for attachment to the handle attachment structures; and, a handle structure. The handles have a rotational movement in the plane and are symmetrically positioned from the centerline of the device.

14 Claims, 5 Drawing Sheets

(58) Field of Classification Search
USPC .................................................. 600/201–245
See application file for complete search history.

(56) References Cited

U.S. PATENT DOCUMENTS

2007/0208227 A1    9/2007  Smith et al.
2008/0077171 A1*   3/2008  Blain .................. A61B 17/025
                                                  606/190

FOREIGN PATENT DOCUMENTS

JP         3129928 U        2/2007
WO    WO 2012/026981 A1    3/2012
WO    WO 2012/040206 A1    3/2012

OTHER PUBLICATIONS

Great Britain Intellectual Property Office, Office Action issued in counterpart Great British Patent Application No. GB2312861.4, mailed on Aug. 21, 2024.
International Bureau, International Search Report in International Application No. PCT/NO2022/050050, mailed May 9, 2022.
International Bureau, Written Opinion of the International Searching Authority in International Application No. PCT/NO2022/050050, mailed May 9, 2022.
Norwegian Patent Office, Norwegian Search Report in Norwegian Application No. 20210268, dated Oct. 28, 2022.
Japanese Patent Office, Office Action in Japanese Patent Application No. 2023-549843, mailed on May 16, 2025.

* cited by examiner

SURGICAL RETRACTOR DEVICE

CROSS-REFERENCE TO RELATED APPLICATIONS

This patent application is the U.S. National Stage of International Patent Application No. PCT/NO2022/050050, filed Feb. 23, 2022, which claims the benefit of Norwegian Patent application No. 20210268, filed Feb. 26, 2021, which are each incorporated by reference.

FIELD OF THE INVENTION

The invention relates to a surgical retractor device, and more specifically the invention relates to a surgical retractor device used in performing surgical exposure.

BACKGROUND OF THE INVENTION

In the field of cardiothoracic surgery, for example by sternotomy or thoracotomy, it is necessary to gain access to the anatomical site of interest by use of a self-retaining retractor. Standard incisions in cardiothoracic surgery include sternotomy and thoracotomy. During the procedure of thoracotomy, a retractor is used to spread ribs and soft tissue apart, thus gaining access to the pleural space. Full or partial sternotomy is performed by a midline incision along the sternum, whereupon the sternal halves are parted by a sternal retractor to provide access to the heart and associated structures. The retractors used in these procedures have jaws which open in a single plane. Albeit any surgical exposure has the potential to provide sufficient access to the chest cavity, the degree and type of exposure needs to be weighed against morbidity as the procedure may put the patient under enormous strain. These procedures are therefore associated with a notable degree of post-operative pain and long patient recovery time.

The force the surgeon applies on the surgical incision, through the device, is variable depending on the angle of the hand-cranked lever due to the design of the Finocheitto retractor. The rotation speed of the hand-cranked lever is not linearly proportional to the opening speed of the arms, leaving the user without a feel for the opening speed and force. One of the downsides to the classical retractor is the absence of force-feedback, making it difficult for the surgeon to judge the amount of force applied when accessing the anatomical site of interest. This means that the surgeon has a limited ability to know how much force is applied. It is an advantage to finely control the opening of the jaws so the operator can avoid unnecessary damage to the bones and tissue during retraction. The operator's ability to fine-tune and feel the force exerted during retraction is absent in classical retractors. The Finochietto retractor comprises moving metal-on-metal parts that requires lubrication to function optimally, if this is not done every time after sterilizing of the device, the device will function sub-optimally. Furthermore, the Finochietto retractor has the rotating lever on one side, wherein the lever transverses with the device as it rotates. Thus, the lever moves along a plane transverse of the surgical incision, causing a greater momentum on the device when operated due to the transverse displacement of the lever during retraction. When the Finochietto retractor is in its open state a bar comprising notches is exposed, and may be located inconveniently. Mainly, the exposed notches may hinder and damage surgical equipment such as tubes and cords and prevent them from moving freely during surgery. Worst-case scenario is when the fragile pacemaker cables are cut off due to the lever-system going over the jammed pacemaker cables.

Finally, following advancements in the field of cardiothoracic surgery, more types of surgical incisions are routinely being performed. Classical retractors have few interchangeable parts and do not necessarily cater to specific preferences of the surgeon or needs of the patient.

Several other types of rib retractors have been developed in order to try to mitigate the downside of the Finochietto retractor.

U.S. Pat. No. 10,603,025 B2 disclose a surgical rib retractor having a housing with a first shoulder and second shoulder 70,74. The retractor further has a first and second arm unit 76, 78 pivotably coupled to the first and second shoulder. The surgical rib retractor also has a first and second arm actuator 80, 82 to pivot first and second arms up and down. Furthermore, the surgical rib retractor of U.S. Pat. No. 10,603,025 B2 has a rotatable knob 84 connected to a single actuator 84 to spread the arms 76, 78.

The downside of the solution disclosed in U.S. Pat. No. 10,603,025 B2 is the same as for the Finochietto retractor, mainly that force is applied through the device in a skewed way by twisting the operating-wheel, hence applying a rotational moment. Moreover, the user must turn the operating wheel the same number of times to close the retractor after surgery, causing uneven forces to be transferred to a patient and slow closing of the device after a surgery is completed.

European Patent EP2080480A1 disclose a sternum retractor device comprising a pair of jaws 1a, 1b; 20a, 20b configured in such a way to be inserted between the two sternal halves and shaped so as to engage firmly on said halves, actuating means 2 comprising a hydraulic cylinder 3 and piston 4 between the pair of jaws 1a, 1b; 20a, 20b. The hydraulic cylinder is actuated by a syringe. The device is not suitable surgical exposure as the actuator and the actuator arms would conceal the surgical site. The use of a syringe to actuate the actuators will not give a user any feedback on the forces applied to the patient. Furthermore, the members that forces the pair of jaws apart comprises hinged and sliding parts that may pinch and damage surgical equipment such as pacemaker wires and tubing.

Document WO 2012040206 A1 discloses a surgical retractor device comprising a first press arm 122 coupled to a pivotal a holder assembly 104, and a second press arm 126 coupled to the holder assembly 104, and a third press arm (316) glideable connected to the holder assembly 104. The solution disclosed in WO 2012040206 A1 exposes all mechanisms to the operation site making it hard to disinfect and exposes the surgical site to moving parts that can pinch and damage the patient and expose the site to non-sterile equipment.

Therefore, it is an aim of the present invention to provide a device that may be operable by one hand and where the forces applied to operate the device is in the same plane as the opening of the arms and wherein the forces applied does not lead to a rotational movement of the device. Furthermore, it is an aim of the present invention to achieve a device that is user-friendly, provides the user with the ability to finetune the device and requires little force to operate and which may be closed in a rapid manner and that will leave the input lever at a stationary location.

It is a further aim of the present invention to provide a device that may provide the user with feedback relating to the force applied.

It is a further aim of the present invention to overcome the shortcomings of the known prior art.

To achieve these objectives, a device according to the independent claims is provided.

SUMMARY OF THE INVENTION

The invention is set forth and characterized in the main claims, while the dependent claims describe other characteristics of the invention.

In a preferred embodiment of the invention the device comprises a housing, a first press arm pivotably coupled to the housing, and a second press arm pivotably coupled to the housing, said first and second arm having a rotational movement in a first plane. Each press arm comprises a gripping member pivoting around an axis at a right angle with the first plane, at the outer end of each press arm, and an attachment means at the inner end of the arm. The housing comprises an opening and closing mechanism comprising, the mechanism comprising rotatable first and second press arm attachment structure for attaching the attachment means of the press arms, symmetrically positioned a distance away from a centerline of the surgical device, to the housing and rotatable first and a second handle attachment structure and a transfer mechanism to transfer rotation from said first and second handle attachment structure to said first and second press arm attachment structure. The device further comprises a first and a second handle for operating the opening and closing mechanism, each handle comprises a handle attachment means at the inner end of the handle for attaching said handles to the first and second handle attachments structures respectively, and a handle structure operable by a user, wherein the first and second handle having a rotational movement in the first plane and being symmetrically positioned a distance away from the centerline of the surgical device and wherein the two handles are pretensioned towards an open state, and wherein opposite rotational movement of the first and second handle towards the centerline causes opposite rotational movement of the first and second press arms away from the centerline.

In another embodiment of the invention transfer mechanism comprises a first and second cam arms each cam arm connected to the first and second handle attachment structure, respectively, and a first and second activation arms each activation arm connected to the first and second arm attachment structure respectively, and a gear train comprising reduction gears and/or a transfer gears connected to a pinion gear, said pinion gear being connected to a worm gear. Wherein the gear train in one end is rotationally coupled to at least one of the first and second cam arm sand wherein the gear train in another end is rotationally coupled to at least one of the first and second activation arms. Whereby the transfer mechanism is adapted to translate rotation movement from at least one of the first and second cam arms to at least one of the first and second activation arms.

In yet another embodiment the of invention the transfer mechanism comprises a first and second cam arms each cam arm connected to the first and second handle attachment structures, respectively, and a first and second activation arms each activation arm connected to the first and second press arm attachment structures respectively, and at least a hydraulic actuator comprising a piston rod and a cylinder wherein the hydraulic actuator in one end is coupled to at least one of the first and second cam arms and wherein hydraulic actuator in another end is coupled to at least one of the first and second activation arms, whereby the transfer mechanism is adapted to translate rotation movement from the first and second cam arms to the first and second activation arms.

In yet another embodiment the of invention transfer mechanism further comprises a further hydraulic actuator comprising a further piston rod and a further cylinder. Wherein the further hydraulic actuator in one end is coupled to the second cam arm and in another end is coupled to the second activation arm, and wherein the hydraulic actuator in one end is coupled to the first cam arm and in another end is coupled to the first activation arm, whereby the transfer mechanism is adapted to translate rotation movement from the first and second cam arms to the first and second activation arms, respectively.

In yet another embodiment the of invention each of the first and second cam arms comprises a protruding surface area adapted for receiving an end surface of the piston rod, and at least a partly tooted area comprising teeth or cogs, wherein the at least partly tooted area of the first and second cam arms intermesh with each other to ensure the first and second handle rotates synchronous in relation to each other.

In yet another embodiment the of invention at least a spring pretension the first and second handles away from each other, towards an open state.

In yet another embodiment the of invention the handle attachment means are releasably attachable, wherein a surface of the handle attachment means is adapted to receive a corresponding surface of the handle attachment structure.

In yet another embodiment the of invention the arm attachment means are releasably attachable, wherein a surface of the arm attachment means is adapted to receive a corresponding surface of the arm attachment structure.

In yet another embodiment the of invention the opening and closing mechanism comprises a release valve switch and a release vale fluidly coupled to the hydraulic actuator, whereby the release valve switch opens said vale to releases pressure in the actuators, whereby the first and second press arms are movable from an open state towards an closed state.

BRIEF DESCRIPTION OF THE FIGURES

These and other characteristics of the invention will become clear from the following description of a preferential form of embodiment, given as non-restrictive examples, with reference to the attached schematic drawings.

DETAILED DESCRIPTION OF THE INVENTION

Figure 1:
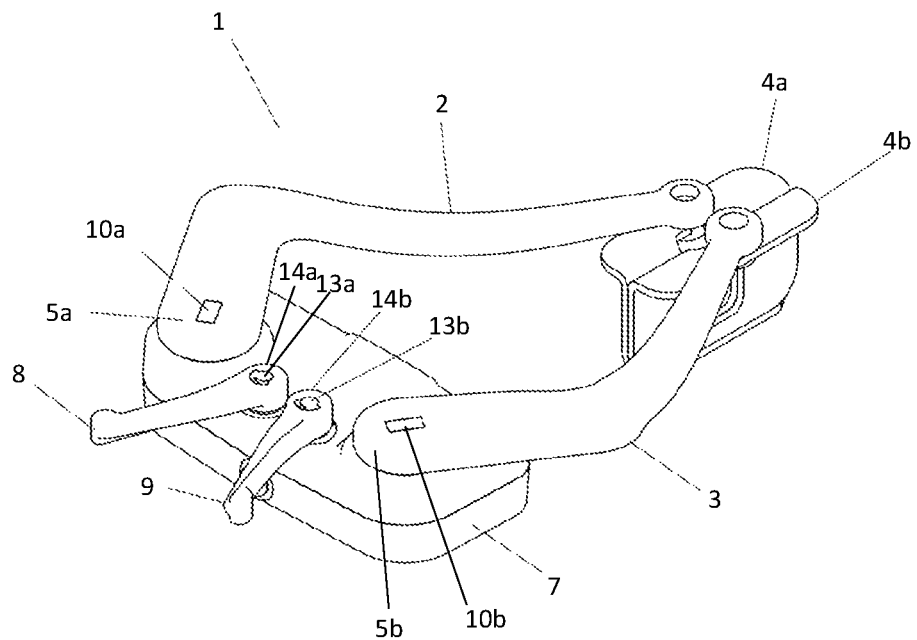
FIG. 1 shows the device in its closed state

The following description will use terms such as "horizontal", "vertical", "lateral", "back and forth", "up and down", "upper", "lower", "inner", "outer", "forward", "rear", etc. A central axis of the instrument is defined to run horizontally along a central axis of the housing and along the centerline between the press arms. The longitudinal direction is defined as the direction along the central axis. These terms generally refer to the views and orientations as shown in the drawings and that are associated with a normal use of the invention. The terms are used for the reader's convenience only and shall not be limiting. Like numerals on different drawings describe the same feature. Numerals with apostrophe represents an additional feature represented by the same numeral, for instance the number 11 will represent one or the first of multiple or all of the multiples, and the numeral 11' represents an additional or a further of the same feature, like a second or multiple of the same feature.

FIG. 1 illustrates a surgical retractor device 1 in its closed state. The device comprises a housing 7, the housing being watertight, and a first press arm 2 pivotably coupled to the housing, and a second press arm 3 pivotably coupled to the housing, said first and second arm 2, 3 having a rotational movement in a first plane. Each press arm comprising a gripping member 4a, 4b, or jaws, pivoting around an axis at a right angle with the first plane, at the outer end of each press arm. The gripping members 4a, 4b is adapted to be inserted into a surgical incision. The pivoting of the gripping members 4a, 4b in relation to the first and second arm 2, 3 ensures the gripping members 4a, 4b always being parallel to the gripping side of the surgical incision when the arms 2,3 are forces apart. The arms further comprise respective attachment means 5a, 5b at the inner end of the arm to releasably attach the arms to the housing 7 or parts thereof. The gripping members 4a, 4b may be interchangeable into different shapes and sizes to cater to different needs. Although illustrated as relatively flat and square shaped, they may be elongated, curved and deeper. The gripping members 4a, 4b may comprise deeper or shallower gripping surfaces to securely grip the surface they are separating.

Figure 2:
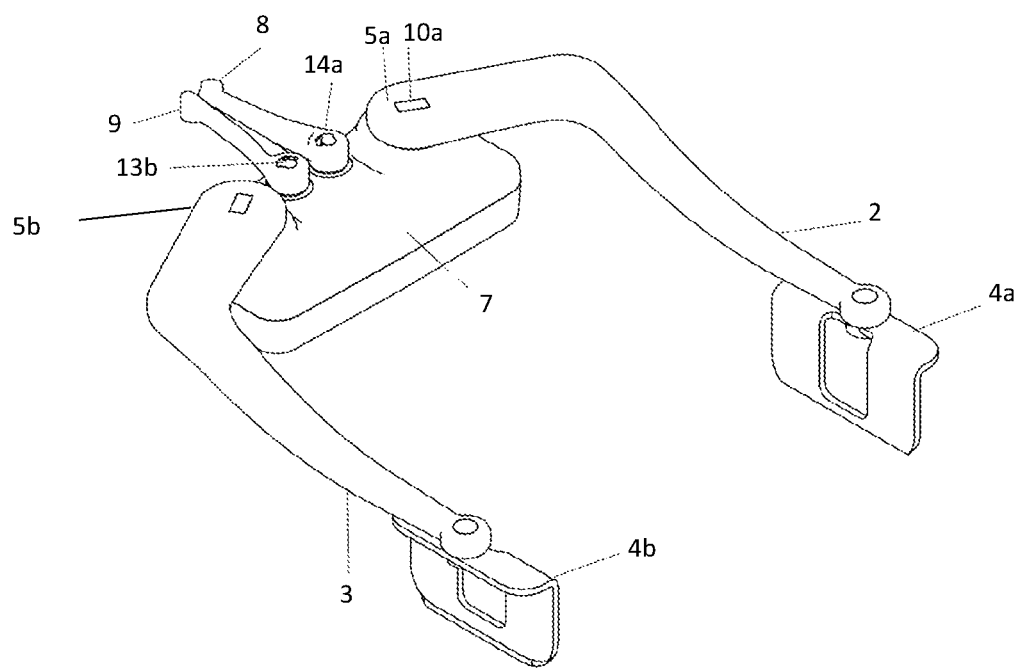
FIG. 2 shows the device in its open state

An opening and closing mechanism 6 is located inside the housing. The housing must be watertight to ease sterilization and to contain impurities like oil, dust and grease from the opening and closing mechanism. For the housing 7 to be watertight the material of the housing may be a watertight material and any opening or excessive may comprise gaskets/and or seals to prevent the intrusion, or extrusion, of any impurities or fluids. The housing may preferably be made of a structural stiff material to contain withstand forces applied to the housing. The purpose of the mechanism 6 is to open and close the press arms 2, 3 in a controllable, accurate and secure manner. In FIG. 2 the device is illustrated in an open state, wherein, the retraction of the press arms 2, 3 exposes the surgical site. The press arms 2, 3 are curved towards a centerline of the device, i.e. each arm having a convex shape with regard to the centerline, thus leaving an operational space in the central region of the chest, or operational location, when the device is in an open position, as illustrated in FIG. 2. Furthermore, all lubrication needed for the device is confined within the housing 7, and any external sterilization of the device will not require relubrication of the opening and closing mechanism 6.

The opening and closing mechanism must be activated by manual operation or a power source controlled by an operator. The mechanism comprising rotatable first and second press arm attachment structures 10a, 10b for attaching the attachment means 5a, 5b of the press arms, symmetrically positioned a distance away from a centerline of the surgical instrument, to the housing 7. The arm attachment means 5a, 5b may be releasable attachable to the arm attachment structures for convenience of sterilizing and cleaning of the device. The arms 2, 3 may be replaced with different lengths arms 2, 3 and with different angles to cater to different needs. The arms 2, 3 may further be angled in both the first plane and in any relation to the first plane. A surface of the arm attachment means 5a, 5b is adapted to receive a corresponding surface of the arm attachment structure 10a, 10b, in a manner not allowing relative rotation. The surface of the arm attachment means 5a, 5b may be a polygonal hollow, or negative, shape and the surface of the arm attachment structure 10a, 10b may be a protruding, or positive, corresponding surface of said first shape, or vise a versa, whereby the positive protrusion may enter into the hole or indent, but not rotate relative to each other in the first plane. The attachments structures and attachments means of both the hands and arms may comprise a securing mechanism, such as a safety pin or locking pin, to secure the attachments.

The opening and closing mechanism further comprise rotatable first and a second handle attachment structure 13a, 13b. Wherein the first and a second handle attachment structure 13a, 13b protrudes from the housing and is adapted to each receive a first and a second handle 8, 9, respectively, for operating the opening and closing mechanism 6. The first and second handles 8, 9 comprises respective handle attachment means 14a, 14b at the inner end of the handle for attaching said handles to the first and second handle attachments structures 13a, 13b, respectively. A surface of the handle attachment means 14a, 14b is adapted to receive a corresponding surface of the handle attachment structure 13a, 13b, in a manner not allowing relative rotation. The handle attachment means 13a, 13b may be releasable attachable to the handle attachment structures for convenience of sterilizing and cleaning of the device, and to change to different shaped handles to cater to the needs of the user. The surface of the handle attachment means 14a, 14b may be a polygonal hollow, or negative, shape and the surface of the handle attachment structure 13a, 13b may be a protruding, or positive, corresponding surface of said first shape, or vise a versa, whereby the positive protrusion may enter into the hole or indent, but not rotate relative to each other in the first plane. Each handle 8, 9 comprises a handle structure which is adapted to be operable by a user with one hand. The attachments structures and attachments means of both the hands and arms may comprise a securing mechanism, such as a safety pin or locking pin, to secure the attachments. Furthermore, the handle attachment means (14a, 14b) may be releasable attachable to the handle attachments structures.

When a user is to transfer the device for a closed first state to an open second state where the press arms 2, 3 are pressed apart the first and second handle is rotated towards each other, whereby an transfer mechanism transfer rotation from the handles 8, 9 operated by a user via said first and second handle attachment structure 13a, 13b and to said first and second press arm attachment structure 10a, 10b. To achieve this the first and second handles 8, 9 has a rotational movement in the first plane and being symmetrically positioned a distance away from the centerline of the surgical instrument. The two handles 8, 9 are pretensioned towards an open state, meaning being positioned relative to each other with at least an positive angle between the handles 8,9, wherein opposite rotational movement of the first and second handles 8,9 towards the centerline causes opposite rotational movement of the first and second press arms 2,3 away from the centerline. Opposite rotational movement of the first and second handles 8,9 should be understood as the movement caused by squeezing or pushing the end of the first and second handles 8, 9 that are not attached to the respective handle attachment structure 13a, 13b, i.e. the outer end, towards each other. The two handles are pretensioned towards an open state and are thus able to cause a pumping action which is transferred to controlled movement of the press arms 2, 3 by the opening and closing mechanism 6. Both handles move symmetrically around a centerline.

Figure 4:
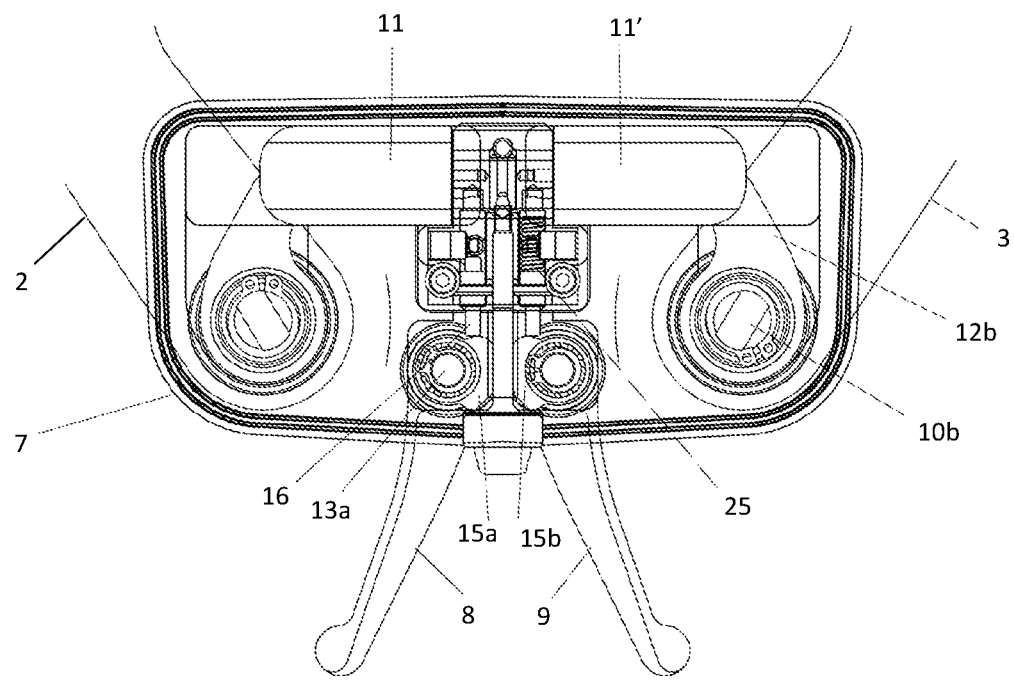
FIG. 4 shows a close view of the housing with the inner workings of the housing exposed
Figure 5:
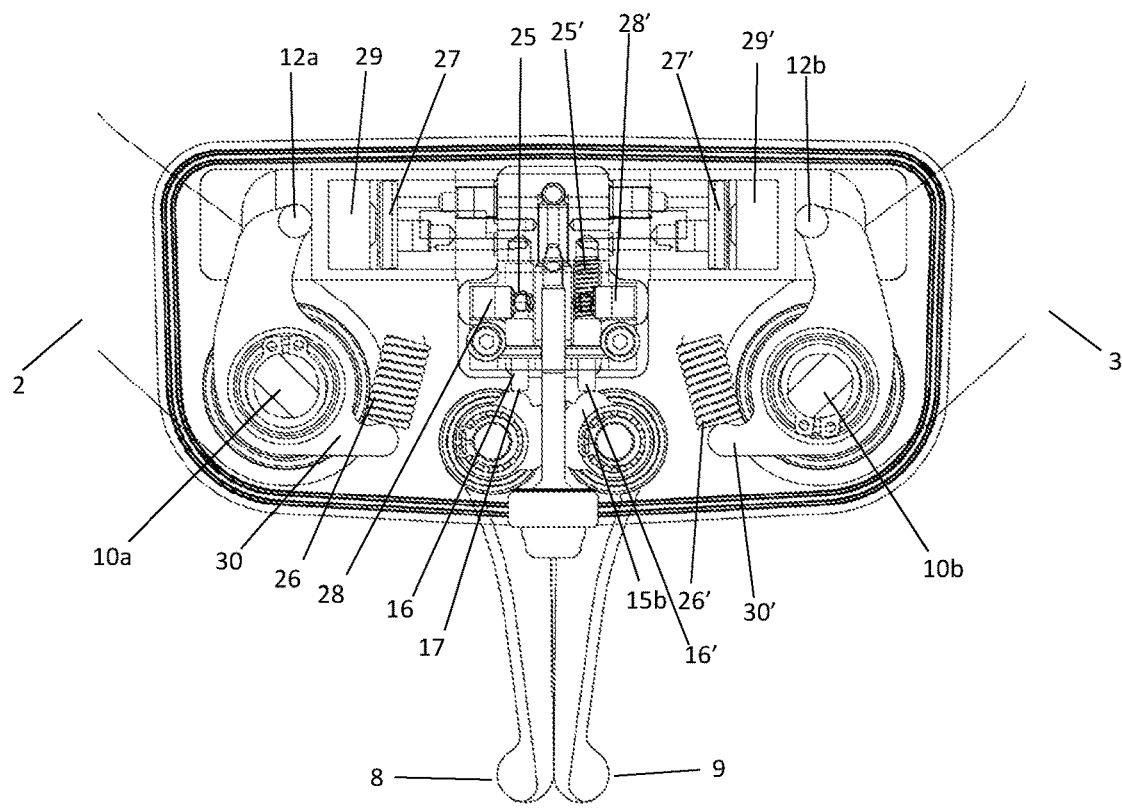
FIG. 5 shows a close view of the housing with the inner workings of the opening and closing mechanism

At least a spring 25 pretensions the first and second handles 8, 9 away from each other, towards the open state. In FIGS. 4 and 5 a spring 25 is situated within the housing 7, surrounding at least a part of the piston rod 16, the piston rod being a movable in is longitudinal directing, and pushes on the piston rod 16 towards the cam arms 15a, 15b, and thereby pushes the first and second handles 8, 9 apart. In an non illustrate embodiment, the spring 25 pushes directly on the cam arms 15a, 15b, and in another embodiment the spring 25 pushes directly on at least one of the first and second handle attachment structures 13, a 13b or at least one of the first and second handles 8, 9 or parts thereof.

As the forces needed to open the device 1 and retract ribs or the sternum of a patient may be greater than what a hand can produce in one closing motion, the devices comprises an transfer mechanism that in an embodiment of the invention transfers and multiplies the force put into the handles 8, 9 to the press arms 2, 3. This means that multiple pushes on the handles 8, 9 will result in the arms being forcibly pressed apart a distance per one push on the first and second handles 8,9. As the force acting from a patient on the arms 2, 3 increases, a user will experience increased resistance on the handle 8, 9 to give the user a tactile and tangible feel of the forces applied to the patient. The mechanism may be a mechanical gear and ratcheting mechanism or it may be a hydraulic mechanism.

Figure 3:
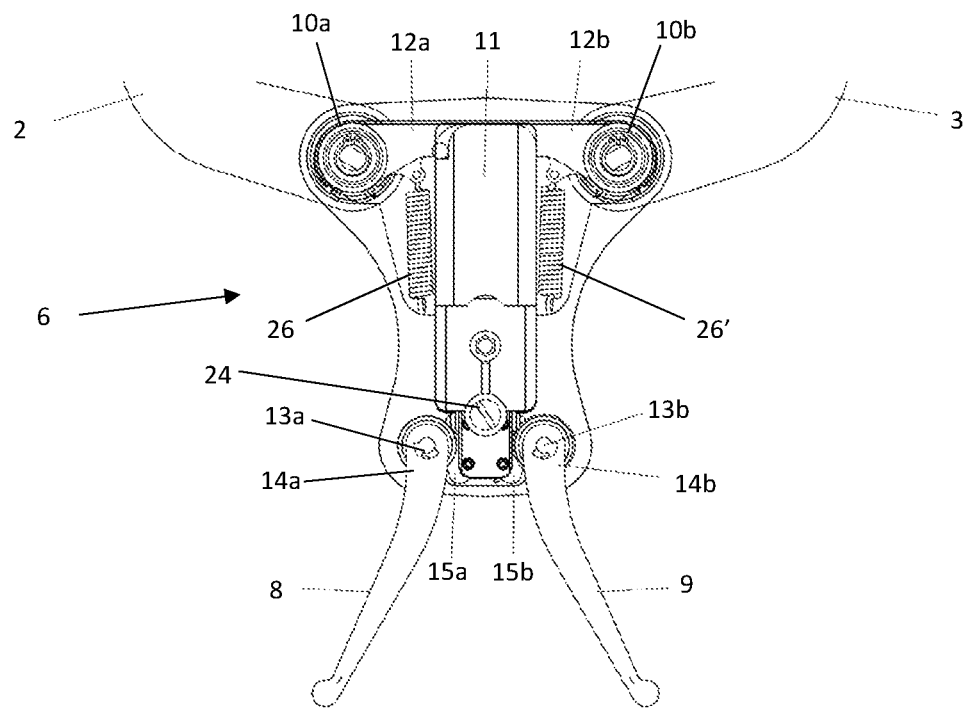
FIG. 3 shows the device with the inner workings of the housing exposed

FIG. 3 shows the device with the inner workings exposed. In FIG. 3 an embodiment of the invention is illustrated where the transfer mechanism comprises first and second cam arms 15a, 15b. Each cam arm is connected to the first and second handle attachment structure 13a, 13b, respectively. This should be understood as the first cam arm 15a is connected to the first handle attachment structure 13a, and the second cam arm 15b is connected to the second handle attachment structure 13b. The cam arms 15a,15b is connected to respective handle attachment structures 13a, 13b in a fixed manner, i.e. not allowing relative rotation between a cam arm and its handle attachment structure, so when a handle attachment structure 13a, 13b is rotated by one of the handles 8, 9 the cam arm also rotates. The transfer mechanism illustrated in FIG. 3 further comprises a first and second activation arms 12a, 12b. Each activation arm is connected to the first and second press arm attachment structure 10a, 10b, respectively. The first and second press arms 2 and 3 are pretensioned towards a closed state i.e. pretensioned to be pressed together. This is achieved by at least an arm spring(s) 26, 26' in one end connected to the housing 7, or parts thereof, and in another and connected at least one of the arm attachment structures 10a, 10b or parts thereof.

In the illustrated embodiment of the invention the mechanism further comprises a hydraulic actuator 18 comprising a piston rod 16 and a cylinder 11. The hydraulic actuator 18 is in one end coupled to, by being seated against, both of the first and second cam arms 15a, 15b, and in another end is coupled to, by being seated against, both of the first and second activation arms 12a, 12b. Whereby the transfer mechanism is adapted to translate rotation movement from the first and second cam arms 15a, 15b to the first and second activation arms 12a, 12b. Each activation arm 12a, 12b is connected to the first and second arm attachment structure 10a, 10b, respectively. This should be understood as the first activation arm 12a is connected to the first arm attachment structure 10a, and the second activation arm 15b is connected to the second arm attachment structure 10b.

The activation arms 12a, 12b is connected to respective arm attachment structure 10a, 10b in a fixed rotational manner, i.e. not allowing relative rotation between a an activation arm and its arm attachment structure, so when the hydraulic actuator 18 extends and pushes on the activation arms 12a, 12b, thereby rotating them about an axis going through the respective attachment structures, the activation arms 12a, 12b are rotated which in turn rotates the rotatable arm attachment structures 10a, 10b and thus presses the press arms 2,3 apart.

FIG. 4 shows the device with the inner workings of the housing 7. In FIG. 4 an embodiment of the invention is illustrated where the transfer mechanism comprises a first and a second hydraulic actuator 18, 18'. When disclosing multiple hydraulic actuators, a hydraulic actuator 18 and one further hydraulic actuator 18' should be understood as equivalent to at least a first hydraulic actuator 18 and a second hydraulic actuator 18'. In the embodiment the actuator comprises a piston rod 16 and a further cylinder 11, and the further hydraulic actuator 18' comprising a further piston rod 16' and a further cylinder 11'. The further hydraulic actuator 18' in one end is coupled to the second cam arm 15b, and in another end is coupled to the second activation arm 12b. The hydraulic actuator 18 in one end is coupled to the first cam arms 15a, and in another end is coupled to the first activation arm 12a. Whereby the transfer mechanism is adapted to translate rotation movement from the first and second cam arms 15a, 15b to the first and second activation arms 12a, 12b, respectively, when the handles 8, 9 are pressed together. In FIG. 4 the first and second handles 8, 9 are illustrated symmetrically spaced apart, which is the handles 8, 9 open state.

FIG. 5 illustrates a detailed view of the transfer mechanism. In the illustrated embodiment of the invention shown in FIG. 5, the transfer mechanism comprises two hydraulic actuators 18, 18'. Each actuator comprises a movable piston rod 16, 16', wherein the piston rod comprises an end surface seated against, and thus movably coupled, to at least one of the respective protruding surface areas 17, 17' of the cam arms 15a, 15b. The opposite end of the piston rods 16, 16 comprises a sealing portion which seals of a hydraulic fluid volume confined by a piston chamber, said piston chamber being in fluid contact with a check valve. The check valve is further fluidly coupled to a fluid volume 29, 29' confined by the main cylinder 11, 11' and a sealing end portion of the main cylinder rod 27, 27 within the main cylinder 11, 11'. Wherein the main cylinder 11, 11' is translational movable in relation to the main cylinder rod 27, 27'. In another non-illustrated embodiment, a cylinder rod pushes on the handle attachment structures 13a, 13b and the main cylinders 11, 11' are stationary.

The method for a user to open the press arms 2, 3 is initiated with a user pressing together the first and second handles 8, 9—said handles being connected to the first and second handle attachment structures 13a, 13b—the first and second cam arms 15a, 15b are rotated, which pushes on the piston rods 16, 16' which causes translational movement of said rods and the hydraulic fluid volume within the piston chamber decreases. At least a part of the hydraulic fluid within the piston chamber is then pushed through the check valve and into the volume 29, 29' in the main cylinders 11, 11'. This cause the cylinders 11, 11' and main cylinder rods 27, 27' to extend in relation to each other—as the hydraulic fluid volume in the main cylinders 11, 11' increases—and the main cylinders 11, 11 pushes away from the cylinder rods 27, 27' towards and against the activation arms 12a, 12b.

Thereby, the arm attachment structures 10a,10b are rotated which opens the press arms 2, 3.

When the handles 8,9 are released, the springs 25, 25' pushes the pistons 16, 16' backwards—causing translational movement of the piston rods 16, 16'—against the cam arms 15a, 15b. This rotates the handles 8, 9 simultaneously with hydraulic fluid is introduced, from a fluid reservoir 28, through a second check valve and into the increasing volume of the piston chamber. An additional squeeze on the handles 8,9 will result in another sequential repetition of the above-mentioned sequence, and the press mars 2, 3 will be pressed apart one further distance. With repeated squeezes on the handles 8, 9 a user may open the press arms 2, 3 to the desired width. During use the handles 8, 9 will remain symmetrical along the centerline. The greater the force applied externally on the press arms, from a surgical wound or similar, the greater the force needed to be applied by a user on the handles. This ensures the user to feel and gauge the forces applied by the arms 2, 3 on a patient or object. In a non-illustrated embodiment of the invention, the device may comprise a strain gauge and/or momentum gage and/or a torque measurement device, to measure force acting on the arms 2, 3 i.e. the resistance from a body acting on the device. The device may furthered comprise a force or momentum indicator, ether as a visual indicator comprising a scale, or as an indicator that stops the handles 8, 9 from being activated when a certain force on the arms 2, 3 is reached. This indication may be achieved by a torque wrench type gauge such as a deflecting beam-type indicator, a slipper type indicator, a click type indicator or an electronic device comprising a strain gauge. Said indication may also indicate the pressure of the hydraulic fluid to indicate the achieved pressure of the press arms 2, 3

The method for a user to return the device 1 to its closed state i.e. to close the press arms 2,3 together, comprises the user to activate a release valve switch 24. The release valve switch 24 is in communication with a release valve, the release valve being fluidly coupled to the main cylinder(s) 11, 11 and the reservoir 28, 28'. When the release valve switch 24 is activated the release valve opens up and the hydraulic fluid flows from the main cylinder(s) 11, 11 and back into the fluid reservoir 28, 28, relisting the fluid pressure within the main cylinder(s) 11, 11. Thereafter, the pretensioned arm springs 26, 16' together with any outside forces that may act upon the arms 2, 3, pulls the arms 2, 3 together. In FIG. 5 the first and second handles 8, 9 are illustrated symmetrically together, which is the handles 8, 9 closed state. The release valve switch 24 and the corresponding release valve ensures smooth and fast closing of the arms 2, 3. The release valve switch 24 can be operated such that the arms 2, 3 parley closes or fully closes, either in one fluid motion or step-vise closing. A user may thereby close the arms 2, 3 partly or fully and thereby engage the handles 8, 9 to open the arms 2, 3 if adjustments is needed. The instant release of the pressure inside the main cylinder(s) 11, 11 by activation of the valve results in an fast closing in the arms 2, 3 which may be beneficial if the device is used for surgery, such that any surgical would is not exposed longer than absolutely necessary.

In FIG. 5 the spring(s) 26, 26' in one end connected to the housing 7 (not shown), or parts thereof, and in another and connected at least one of the arm attachment structures 10a, 10b via attachment means 30, 30' protruding from the arm attachment structures 10a, 10b.

In FIG. 3 and embodiment of the invention which uses one hydraulic actuator 18 is illustrated. The transfer mechanism for said embodiment may comprise the same features as the above disclosed embodiment illustrated in FIG. 5, but with one hydraulic actuator 18, comprises a movable piston rod 16 wherein the piston rod comprises an end surface seated against, and thus movably coupled, to at least one of the respective protruding surface areas 17, 17' of the cam arms 15a, 15b. The opposite end of the piston rods 16 comprises a sealing portion (not shown) which seals of a hydraulic fluid volume confined by a piston chamber, said piston chamber being in fluid contact with a check valve. The check valve is further fluidly coupled to a fluid volume confined by the main cylinder 11 and a sealing end portion of the main cylinder rod (not shown) within the main cylinder 11. Wherein the main cylinder 11, is translational movable in relation to the main cylinder rod 27.

Figure 6:
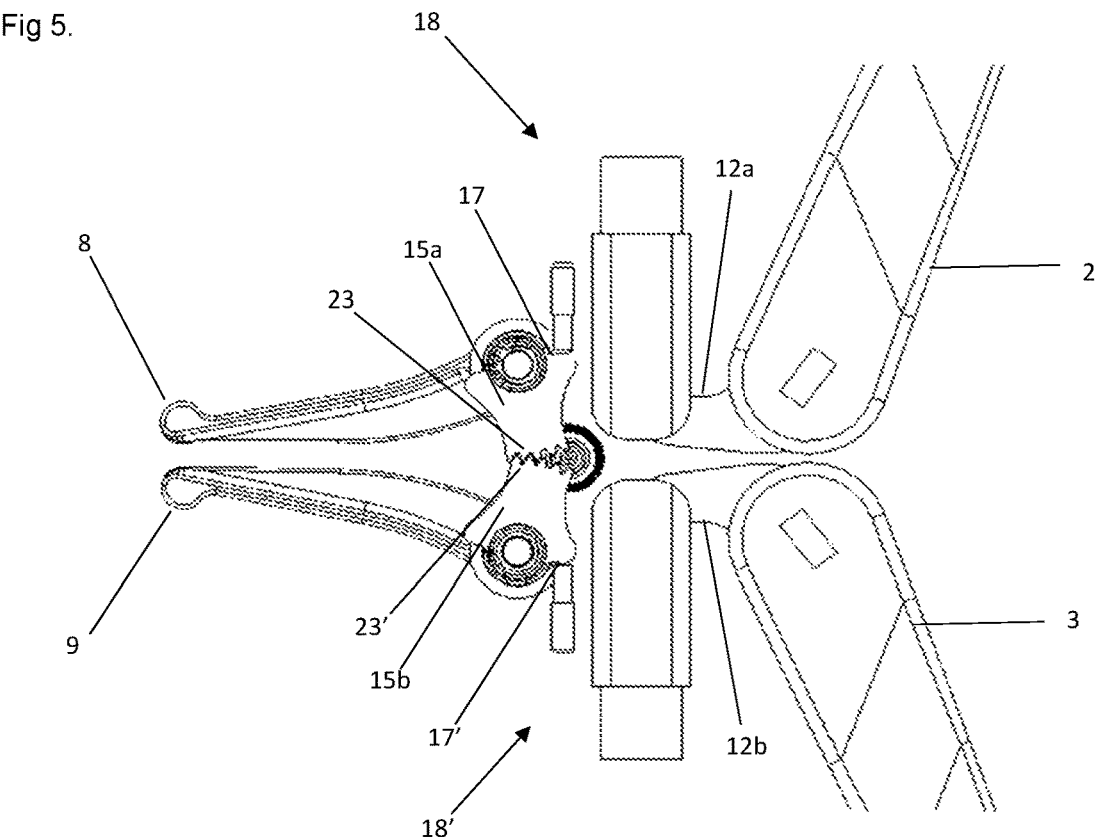
FIG. 6 shows a close view of the inner workings of the opening and closing mechanism

FIG. 6 shows the device with the inner workings of the housing 7 in an embodiment of the invention wherein the invention comprises means to ensure that a user rotates the first and second handle 8,9 at the same rate and distance. This will ensure that press arms 2, 3 are opened at the same rate and the same distance from the centerline. A user may use both left or right hand to operate the device and the device shall not favor any hand, as would be the case if a handle was stationary in relation to the other. To ensure that an even pressure is translated from both hands to the press arms 2, 3 through the transfer mechanism, each of the first and second cam arms 15a, 15b comprises at least a partly tooted areas 23, 23' comprising teeth or cogs. The respective partly tooted areas 23, 23' protrudes a distance away from the handle attachment structures 13a, 13b, and wherein the at least partly tooted areas 23, 23' of the first and second cam arms 15a, 15b intermesh with each other to ensure the first and second handle 8, 9 rotates synchronous in relation to each other.

Figure 7:
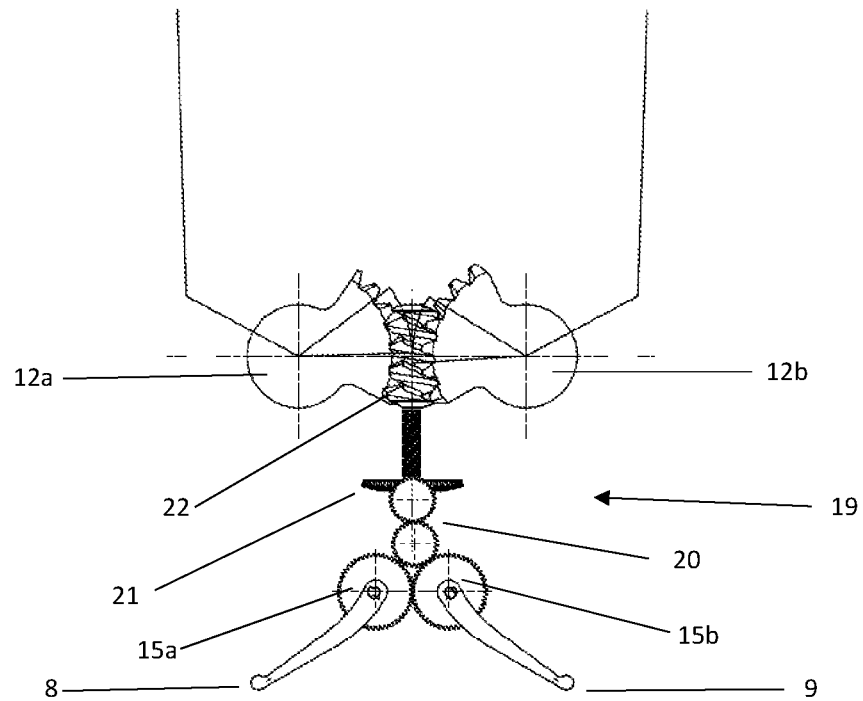
FIG. 7 shows a close view of the gear train of the opening and closing mechanism

In FIG. 7 it is further illustrated that each of the first and second cam arms 15a, 15b comprises respective protruding surface areas 17, 17' adapted for receiving an end of the hydraulic actuators 18, 18'. In the illustrated example the hydraulic actuators 18, 18' each comprises an end surface on the piston rods 16, 16' adapted to be seated against, and thus movably coupled, to the protruding surface areas 17, 17' of the cam arms 15a, 15b.

FIG. 7 shows the device with the inner workings of the housing 7 in an alternative embodiment of the invention wherein the transfer mechanism comprises a gear train 19, said gear train 19 comprises reduction gears and/or a transfer gears 20 connected to a pinion gear 21, said pinion gear being connected to a worm gear 22. The gear train 19 is in one end rotationally coupled to at least one of the first and second cam arms 15a, 15b via circumferential toothed areas 23, 23'. The gear train 19 is in another end rotationally coupled to at least one of the first and second activation arms 12a, 12b, wherein the at least one of the first and second activation arms 12a, 12b comprises a toothed section corresponding to a worm gear screw. The transfer mechanism comprising the gear train 19 is adapted to translate rotation movement from at least one of the first and second cam arms 15a, 15b to at least one of the first and second activation arms 12a, 12b. The handle attachment structures may comprise a pawl and ratchet mechanism (not shown) for repeated squeezing of the handles to open the press arms 2, 3.

Figure 8:
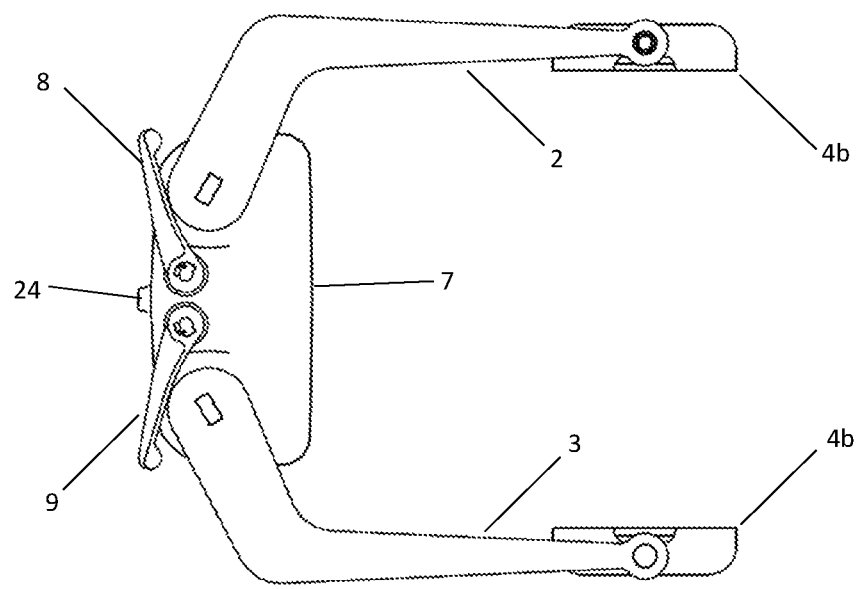
FIG. 8 shows the device with handles in an open state.

In FIG. 8 the device 1 is illustrated with the first and second handle 8, 9 in their fully open position, whereby the handles are opened up fully or partly folded over or under the housing 7. Thus, the handles minimally protrude the edge of the housing and are thereby not hindering or catching any surgical equipment such as tubes and wires, if used for said purpose.

Figure 9:
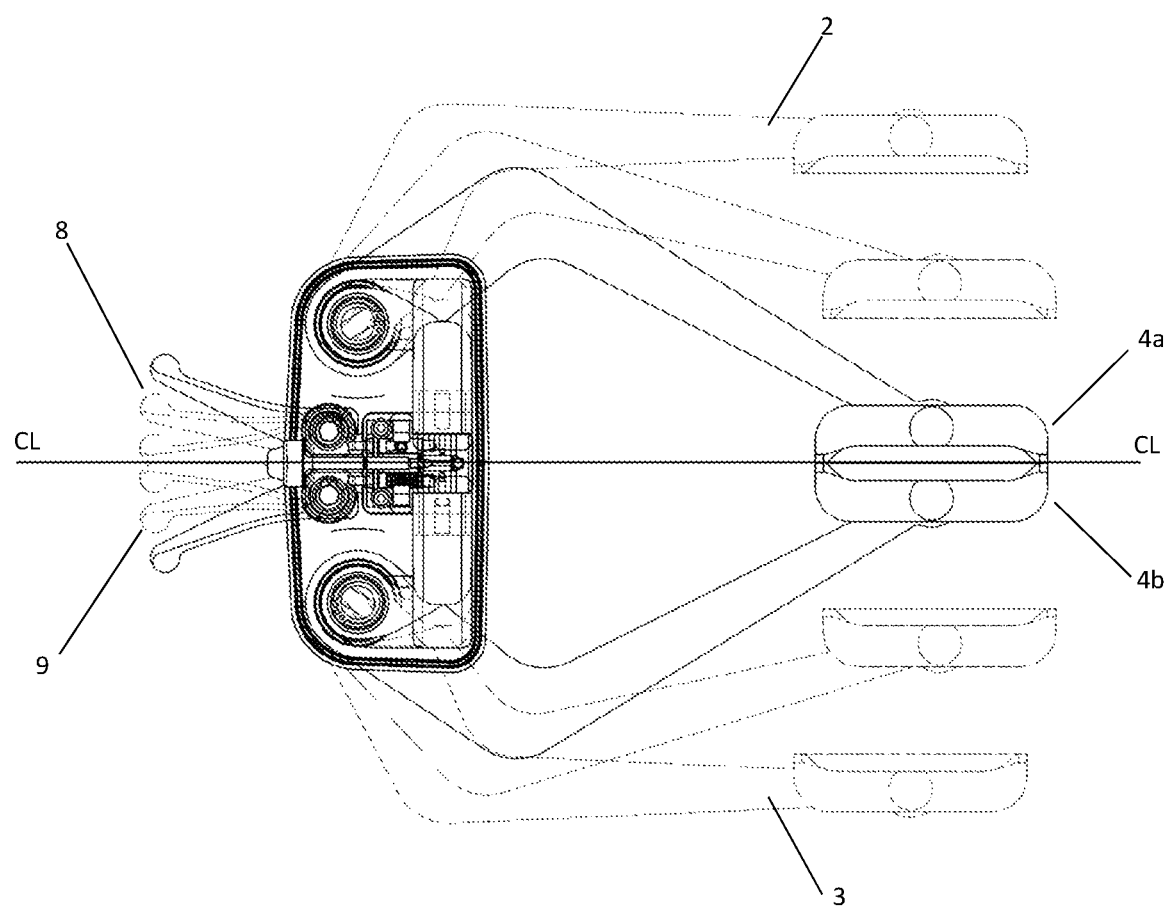
FIG. 9 shows the device in multiple states.

FIG. 9 illustrates the device in a fully closed state, a fully opened state a partly opened and closed state where in press arms 2, 3 are between the opened and closed state. In FIG. 8 the centerline CL is illustrated, wherein the arms 2, 3 are symmetrically positioned around the centerline in the open state and wherein the gripping members 4a, 4b meet at the centerline in the closed state.

Although not illustrated, the handle attachment structures 13a, 13b and arm attachment structures 10a, 10b, and thus the arms 2, 3 and the handles 8, 9, may both protrude the housing 7 on the same side of the housing, either on a upward facing side or on a downward facing side, or they may be protruding the housing 7 on opposing sides, such that the arm attachment structures 10a, 10b protrudes the housing 7 on a upward facing side and the arm attachment structures 10a, 10b on the downwards facing side, or visa versa. Such that both the arms 2, 3 and the handles may be positioned as to not be to hinder the movement of a user and a be out of the way for any tubes or cords used for other means. The arms 2, 3 and handles 8, 9 may also extend form side portions of the housing 7.

Although specific embodiments of the invention have been described and illustrated herein, it is recognized that modifications and variations may readily occur to those skilled in the art, and consequently, it is intended that the claims be interpreted to cover such modifications and equivalents.

REFERENCE NUMERALS P33138NO00

1 Surgical retractor instrument
2 first press arm
3 second press arm
4a, 4b gripping member
5a, 5b arm attachment means
6 opening and closing mechanism
7 housing
8 first handle
9 second handle
10a, 10b arm attachment structure
11, 11' main cylinder(s)
12a, 12b first and second activation arms
13a, 13b handle attachment structure
14a, 14b handle attachment means
15a, 15b first and second cam arms
16, 16' piston rod(s)
17, 17' protruding surface area on cam(s)
18, 18' hydraulic actuator(s)
19 gear train
20 gear
21 pinion gear
22 worm gear
23, 23' tooted area(s)
24 release valve switch
25 lever spring(s)
26 arm spring(s)
27, 27' main cylinder rod (5)
28, 28' hydraulic fluid reservoir(s)
29, 29' fluid volume(s) confined within the main cylinder
30, 30' spring attachment means(s)

The invention claimed is:

1. A surgical retractor device comprising: a housing; a first press arm pivotably coupled to the housing, and; a second press arm pivotably coupled to the housing; said first press arm and second press arm each having a rotational movement in a first plane; each first and second press arm comprising: a gripping member pivoting around an axis at a right angle with the first plane, at an outer end of the press arm, an arm attachment means at an inner end of the press arm, wherein the housing comprises: an opening and closing mechanism, the opening and closing mechanism comprising: a rotatable first press arm attachment structure and a rotatable second press arm attachment structure for attaching the arm attachment means of the first and second press arms, symmetrically positioned a distance away from a centerline of the surgical retractor device, to the housing, and; a rotatable first handle attachment structure and a rotatable second handle attachment structure, and; a transfer mechanism to transfer rotation from said rotatable first and second handle attachment structure to said rotatable first and second press arm attachments wherein the surgical retractor device further comprises a first handle and a second handle for operating the opening and closing mechanism, each first and second handle comprising: a handle attachment means at an inner end of the handle for attaching said handle to the first and second handle attachment structures, respectively, and; a handle structure operable by a user, the first handle and the second handle each having a rotational movement in the first plane and being symmetrically positioned a distance away from the centerline of the surgical device, and; wherein the first and second handles are pretensioned towards an open state, and; wherein opposite rotational movement of the first and second handles towards the centerlines causes opposite rotational movement of the first and second press arms away from the centerline.

2. The surgical retractor device according to claim 1, wherein the transfer mechanism comprises: a first cam arm and a second cam arm each first and second cam arm connected to the rotatable first and second handle attachment structure respectively, and; a first activation arm and a second activation arm each first and second activation arm connected to the rotatable first arm and second arm attachment structure, respectively, and; a gear train comprising reduction gears and/or a transfer gear connected to a pinion gear, said pinion gear being connected to a worm gear, wherein the gear train in one end is rotationally coupled to at least one of the first and second cam arms, and; wherein the gear train in another end is rotationally coupled to at least one of the first and second cam arms to at least one of the first and second activation arms.

3. The surgical retractor device according to claim 2, wherein at least a spring pretensions the first and second handles away from each other, towards an open state.

4. The surgical retractor device according to claim 2, wherein the handle attachment means are releasably attachable, wherein a surface of the handle attachment means is adapted to receive a corresponding surface of the first and second handle attachment structures.

5. The surgical retractor device according to claim 2, wherein the arm attachment means are releasably attachable, wherein a surface of the arm attachment means is adapted to receive a corresponding surface of the first and second press arm attachment structures.

6. The surgical retractor device according to claim 1, wherein the transfer mechanism comprises: a first cam arm and a second arm each first and second cam arm connected to the rotatable first and second handle attachment structures respectively, and; a first and a second activation arm connected to the rotatable first and second press arm attachment structures respectively, and; at least a hydraulic actuator comprising a piston rod and a cylinder, wherein the hydraulic actuator in one end is coupled to at least one of the first and second cam arms, and; wherein the hydraulic actuator in another end is coupled to at least one of the first and second activation arms, wherein the transfer mechanism is adapted to translate rotation movement from the first and second cam arms to the first and second activation arms.

7. The surgical retractor device according to claim 6, wherein the transfer mechanism further comprises: a further hydraulic actuator comprising a further piston rod and a further cylinder, wherein the further hydraulic actuator in one end is coupled to the second cam arm, and in another end is coupled to the second activation arm, and; wherein the hydraulic actuator in one end is coupled to the first cam arm, and in another end is coupled to the first activation arm, wherein the transfer mechanism is adapted to translate rotation movement from the first and second cam arms to the first and second activation arms, respectively.

8. The surgical retractor device according to claim 7, wherein each of the first and second cam arms comprises: a protruding surface area adapted for receiving an end surface of the piston rod, and; at least a partly toothed area comprising teeth or cogs, wherein the at least partly toothed area of the first and second cam arms intermesh with each other to ensure the first and second handles rotate synchronous in relation to each other.

9. The surgical retractor device according to claim 7, wherein the opening and closing mechanism comprises a release valve switch and a release valve fluidly coupled to the hydraulic actuator, whereby the release valve switch opens said valve to release pressure in the actuator(s) wherein the first and second press arms are movable from an open state towards a closed state.

10. The surgical retractor device according to claim 6, wherein each of the first and second cam arms comprises: a protruding surface area adapted for receiving an end surface of the piston rod, and; at least a partly toothed area comprising teeth or cogs, wherein the at least partly toothed area of the first and second cam arms intermesh with each other to ensure the first and second handles rotate synchronous in relation to each other.

11. The device according to claim 6, wherein the opening and closing mechanism comprises a release valve switch and a release valve fluidly coupled to the hydraulic actuator, whereby the release valve switch opens said valve to release pressure in the actuator wherein the first and second press arms are moveable from an open state towards a closed state.

12. The surgical retractor device according to claim 1, wherein at least a spring pretensions the first and second handles away from each other, towards an open state.

13. The surgical retractor device according to claim 1, wherein the handle attachment means are releasably attachable, wherein a surface of the handle attachment means is adapted to receive a corresponding surface of the first and second handle attachment structures.

14. The device according to claim 1, wherein the arm attachment means are releasably attachable, wherein a surface of the arm attachment means is adapted to receive a corresponding surface of the first and second press arm attachment structures.

* * * * *